US008570500B2

(12) United States Patent
Javadi et al.

(10) Patent No.: US 8,570,500 B2
(45) Date of Patent: Oct. 29, 2013

(54) DETECTOR ARRANGEMENT FOR A FLOW CYTOMETRY SYSTEM

(75) Inventors: Shervin Javadi, Monte Sereno, CA (US); Arjuna Karunaratne, Fremont, CA (US)

(73) Assignee: Stratedigm, Inc., San Jose, CA (US)

( * ) Notice: Subject to any disclaimer, the term of this patent is extended or adjusted under 35 U.S.C. 154(b) by 308 days.

(21) Appl. No.: 12/860,790

(22) Filed: Aug. 20, 2010

(65) Prior Publication Data

US 2012/0044480 A1  Feb. 23, 2012

(51) Int. Cl.
| G01N 21/00 | (2006.01) |
| G01N 1/10 | (2006.01) |
| G01J 3/28 | (2006.01) |

(52) U.S. Cl.
USPC .............. 356/73; 356/246; 356/328; 356/337

(58) Field of Classification Search
USPC .......................................... 356/328, 246, 337
See application file for complete search history.

(56) References Cited

U.S. PATENT DOCUMENTS

| 3,584,920 | A | * | 6/1971 | Sills | 327/497 |
| 4,573,796 | A | * | 3/1986 | Martin et al. | 356/318 |
| 5,682,038 | A | * | 10/1997 | Hoffman | 250/458.1 |
| 5,760,900 | A | | 6/1998 | Ito | |
| 7,440,101 | B2 | | 10/2008 | Auer | |
| 7,692,773 | B2 | | 4/2010 | Roth | |
| 2006/0273260 | A1 | | 12/2006 | Casstevens | |

FOREIGN PATENT DOCUMENTS

| JP | 2007-46947 A | 2/2007 |
| JP | 2007046947 A | 2/2007 |

OTHER PUBLICATIONS

International Search Report and Written Opinion dated Mar. 28, 2012 in PCT Application No. PCT/US2011/048649.
International Search Report mailed on Mar. 28, 2012 for PCT Patent Application No. PCT/US2011/048649, 5 pages.
Written Opinion of the International Searching Authority mailed on Mar. 28, 2012 for PCT Patent Application No. PCT/US2011/048649, 5 pages.

* cited by examiner

*Primary Examiner* — Tarifur Chowdhury
*Assistant Examiner* — Sunghee Y Gray
(74) *Attorney, Agent, or Firm* — Kilpatrick Townsend & Stockton LLP

(57) ABSTRACT

Systems and methods for regarding a cytometry system are disclosed. The system can include a plurality lasers which are spatially separated from each other. Each laser can be assigned to a single detector. The single detector can process multiple events from each laser by digital switching of signal processing circuitry. Additional detectors can be assigned to receive light in a similar manner.

22 Claims, 5 Drawing Sheets

DETECTOR ARRANGEMENT FOR A FLOW CYTOMETRY SYSTEM

BACKGROUND OF THE INVENTION

The invention is related to flow cytometry systems, and more specifically, detector arrangements for flow cytometry systems.

Flow cytometry systems are used to analyze aspects of microscopic particles, such as cells or cell sized particles. A typical flow cytometry system includes a laser aligned with a flow stream of the microscopic particles. The laser is arranged to emit a beam of light of a single wavelength at the particle which is moving in a hydrodynamically-focused stream of fluid. Typically, a number of detectors collect forward scattered, side scattered, and fluoresced light caused by the intersection of the laser beam and particle. Information derived from the collected light can be used to produce histograms, which provide physical and chemical characteristics of the particles.

Complex cytometry systems typically make use of multiple detectors which provide electrical signals derived from the collected light. The detectors are mounted to emissions modules, with each module being mechanically affixed to a particular laser via fiber optics or a pin hole arrangement. The module can provide a certain filtered wavelength of light to each detector via optics. Thus, each detector is mechanically affixed to a particular laser, and each laser requires an emissions module. When it is desired to process multiple events caused by multiple lasers, then a complex system is required, as scaling up measurement capabilities requires the addition of many detectors. Accordingly, current multiple laser cytometry systems often possess little flexibility, large size, and high cost.

BRIEF SUMMARY OF THE INVENTION

Embodiments of the invention provide a cytometry system that includes a computing system. A plurality of lasers may be controlled by the computing system to emit laser light. Each laser may be spatially separated along a flow stream path. A light condenser may collect a plurality of light pulses that are by time of flight intervals. Each light pulse may be derived from the spatially separated laser light intersecting material flowing in the flow stream path. A first detector may be configured to receive the plurality of light pulses from the light condenser. The first detector may be coupled to sampling circuitry. The computing system may be configured to operate the sampling circuitry to process each light pulse according to the time of flight intervals.

In one aspect of the cytometry system, the lasers may emit different wavelengths of laser light with respect to each other.

In one aspect of the cytometry system, at least one laser can include a plurality of collinear lasers.

In another aspect of the cytometry system, the computing system may be configured to turn the sampling circuitry ON for pre-determined sampling intervals between the time of flight intervals and OFF during the time of flight intervals.

In another aspect of the cytometry system, the time of flight intervals may be determined from flow rate of the material and the distance between the spatially separated lasers.

In another aspect of the cytometry system, the sampling circuitry may be configured to only process a signal of a light pulse during the pre-determined sampling interval.

In another aspect of the cytometry system, the sampling circuitry may be configured to discharge one or more energy storage elements at some time point when the signal of each light pulse is not being sampled.

In another aspect of the cytometry system, a second detector may be configured to receive at least a portion of the plurality of light pulses from the light condenser, the second detector being coupled to its own sampling circuitry In another aspect of the cytometry system, the computing system may be configured to turn respective sampling circuitries of the first and second detector ON between the time of flight intervals and OFF during the time of flight intervals.

In another aspect of the cytometry system, the respective sampling circuitries may be configured to discharge one or more energy storage elements of the respective sampling circuitry at some time point when the signal is not being sampled.

In another aspect of the cytometry system, the respective sampling circuitries may be configured to process the respective signals by triggering pulse width integrators, logarithmic and linear pulse peak detectors, and logarithmic and linear pulse area integrators of respective signal processing circuitries.

In another aspect of the cytometry system, the respective signals may be digitally converted before or after being processed by the respective signal processing circuitries.

Embodiments of the invention also provide a method for operating a cytometry system. In the method, a first light pulse signal derived from a first laser interacting with a material may be received. Further, a first ON signal may be triggered over the duration of a first predetermined sampling interval. Pulse information may be derived from the first light pulse signal during the first ON signal via signal processing circuitry. An OFF signal may be triggered to stop the signal processing circuitry from deriving pulse information from the first light pulse signal. The OFF signal may correspond to a time of flight interval of the material between the first laser and a spatially separated second laser. A second light pulse signal derived from the second laser interacting with the material may be received. A second ON signal may be triggered over the duration of a second predetermined sampling interval. Pulse information may be derived from the second light pulse signal during the second ON signal.

In one aspect of the method, the first light pulse signal may be amplified using a first amplifying circuit.

In another aspect of the method, the second light pulse signal may be amplified using a second amplifying circuit.

In another aspect of the method, at least one energy storing filter element of the signal processing circuitry may be charged from the first light pulse signal during the first ON signal.

In another aspect of the method, the at least one energy storage filter element includes a capacitor, inductor, or a processor or computer readable medium including a digital implementation of a filter.

In another aspect of the method, the at least one energy storage filter element is discharged during the OFF signal.

In another aspect of the method, the at least one energy storing filter element of the signal processing circuitry may be recharged from the second light pulse signal during the second ON signal.

In another aspect of the method, the time of flight interval may be derived from a flow rate of the material between the spatial separation of the first laser and the second laser.

In another aspect of the method, deriving pulse information from the first and second light pulse signals may respectively include triggering pulse width integrators, pulse peak detectors, and pulse area integrators of the signal processing circuitry.

In another aspect of the method, the pulse information respectively derived from the first and second light pulses may be converted to digital signals.

Embodiments of the invention also provide a machine readable medium containing software code which, when executed by a processor, can cause the processor to perform at least one of the methods disclosed herein.

Embodiments of the invention also provide a system including the processor coupled by a communications bus to the machine readable medium.

These and other embodiments of the invention are described in further detail below, which provides an exemplary implementation of the embodiments and aspects disclosed herein.

DETAILED DESCRIPTION OF THE INVENTION

Figure 1:
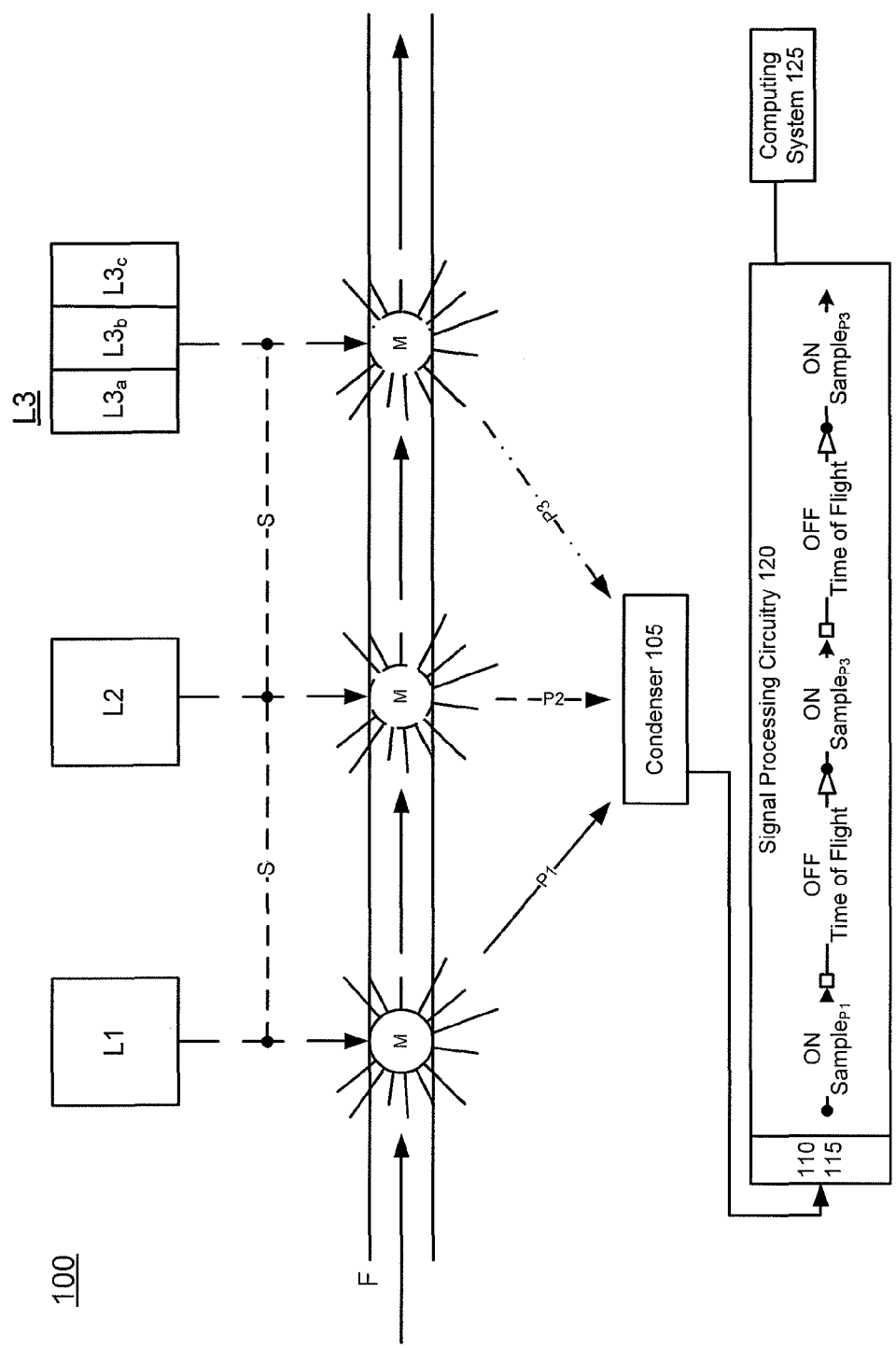
FIGS. 1 and 2 are simplified schematic views of cytometry systems, according to respective embodiments of the invention.

FIG. 1 shows a simplified cytometry system 100, according to an embodiment of the invention. It should be understood that certain aspects (e.g. optics, emissions modules) common to flow cytometry systems are not included for the sake of brevity. The system 100 includes a plurality of lasers L1, L2, L3. The lasers L1, L2, L3 can be configured to emit different wavelengths of laser light at different power levels. Some exemplary wavelengths include 488 nm (40 mW), 640 nm (50 mW), 405 nm (50 mW), 372 nm (20 mW), 561 nm (50 mW), and 532 nm (50 mW). It should be understood that while only three lasers are shown, more or less may be utilized by the system 100.

The lasers L1, L2, L3 are spatially separated, as indicated by distance S, along a flow stream path F. The flow stream path F is a fluid passage for transportation of material M, which may be an individual biological cell-sized particle or a biological cell. The flow stream F may be sized to only allow one individual portion of material M to occupy the cross-section of the flow stream path F. In some embodiments, the system may hydrodynamically focus (i.e., funnels) under pressure a plurality of the material M into the flow stream F so that only one individual portion of material M is passed into the flow stream F at a time. In other embodiments, hydrodynamic focusing is not implemented, and a simple flow stream is used.

The lasers L1, L2, L3 are configured to emit laser light at the flow stream F at respective interrogation points. At these interrogation points laser light intersects the material M, for example at a 90° angle. A light condenser lens 105 collects side scattered, and/or fluoresced pulses of light P1, P2, P3 that are derived from the intersection of laser light and the material M. Accordingly, each pulse of light P1, P2, P3 may include a plurality of different directional intensities and/or wavelengths. The pulses of light are routed from the light condenser lens 105 to a single detector 110. The light condenser lens 105 can be constructed from multiple lens elements to collect the side scattered, and/or fluoresced pulses of light from the interrogation points, as is known in the art. In some embodiments the light condenser lens 105 is constructed from six lens elements. It should be understood that pulses P1, P2, P3, while shown simultaneously, actually occur at distinct instances of time, with P1 occurring first, P2 second, and P3 last. It should also be understood that a laser as described herein may include a plurality of lasers which are all configured to emit respective laser light at a single interrogation point. This is shown by laser L3, which includes three collinear lasers $L3_a$, $L3_b$, $L3_c$, each of which are configured to emit laser light at the same interrogation point, in a contemporaneous or non-contemporaneous manner with respect to one another. Put another way, each collinear laser $L3_a$, $L3_b$, $L3_c$ can be operated to simultaneously fire at the material M, or fire in rapid succession at the same material M. Each collinear laser $L3_a$, $L3_b$, $L3_c$ can also be configured to emit different wavelengths of laser light with respect to one another. Accordingly, pulse P3 can include multiple pulses derived from different wavelengths of light generated by the collinear lasers $L3_a$, $L3_b$, $L3_c$. In embodiments where the collinear lasers $L3_a$, $L3_b$, $L3_c$ are operated in a non-contemporaneous manner pulse P3 can include multiple wavelengths of light that occur at different times but derived from the same portion of material M. Put another way pulse P3 can include a plurality of phase shifted pulses, respectively derived from the collinear lasers $L3_a$, $L3_b$, $L3_c$ firing in quick succession against a single portion of matter. The collinear lasers $L3_a$, $L3_b$, $L3_c$ may allow for the excitation and emission of fluorophores of different wavelengths, so as to allow later discrimination by color filtering to multiple detectors of time coincident or time separated pulses.

The single detector 110 is configured to receive the pulses of light P1, P2, P3 derived from the plurality of lasers L1, L2, L3 at distinct time intervals, according to when the pulses of light P1, P2, P3 are generated and received. The single detector 110 may be a photodiode or a photo multiplier tube. The single detector 110 is coupled to a receiving circuit 115 which includes associated amplifying and triggering circuitry. The arrival of pulse P1 to the single detector 110 creates one or more pulse signals (e.g., voltage, current) that may be proportionally derived from pulse P1. In embodiments where collinear lasers are used, the pulse signal can include a plurality of sub-pulse signals of different wavelengths and/or different phases, which are derived from different lasers. The pulse signal can be amplified and adjusted by the receiving circuit 115, which further causes the occurrence of at least two triggering events. The first triggering event is to switch ON gated sampling circuitry 120 that is coupled to the receiving circuit 115. The gated sampling circuitry 120 includes pulse width integrators, logarithmic and linear pulse peak detectors, and logarithmic and linear pulse area integrators. The gated sampling circuitry 120 may then process the amplified pulse P1 accordingly and pass it on to a computing system 125 for further processing (e.g. histogram generation). The computing system 125 is electronically coupled to all aspects of the system 100 for operational control thereof.

The second triggering event occurs when a predetermined duration for sampling the pulse signal of pulse P1 has ended, which triggers the gated sampling circuitry 120 to be switched OFF. This second triggering event may trigger a signal to discharge stored energy within energy storing filter elements (e.g., capacitor, inductor) of the gated sampling circuitry 120, when the gated sampling circuitry 120 is OFF. This can be an important step, as the pulse signal generated from pulse P1 may vary greatly in magnitude to pulse signal of pulse P2. Accordingly, aspects of the pulse signal of pulse P1 stored in the energy storing filter element may otherwise mask a pulse signal of pulse P2 within the gated sampling circuitry 120, resulting in a faulty measurement. After discharging, a subsequent pulse will generally recharge the energy storing filter element. The energy storing filter element can include a computer readable medium or processor containing a software algorithm for a digital implementation of the filter. In some embodiments, discharging the filter occurs from resetting memory elements for IIR (infinite impulse response) or FIR (Finite Impulse Response). Accordingly, it should be understood that "energy storing filter element" for the purposes of this disclosure includes a computer implemented filter, as well as traditional electrical components.

The second triggering event is timed to occur when the signal of P1 is not being sampled, e.g., during the time of flight of the material M between pulse P1 and pulse P2. The time of flight is known and constant, and is calculated from the flow rate of the material M and the fixed distance S of the spatial separation between the interrogations points of L1 and L2. When M arrives at the interrogation point of L2, the process may then repeat, and so on at the interrogation point of L3.

It should be understood, that in some embodiments, triggering events can be timed to occur during the time of flight of the material M between respective pulses of light P1, P2, P3. Put another way, the duration of the sampling periods may be offset from the duration of the pulse signals. The sampling periods, i.e., when the gated sampling circuitry 120 is ON, may be fully or partially offset with the pulse signals. Such embodiments can be useful for detecting different light pulse signals which do not occur during the primary excitation of a portion of material, e.g., sampling of a delayed fluorescence signal.

Figure 2:
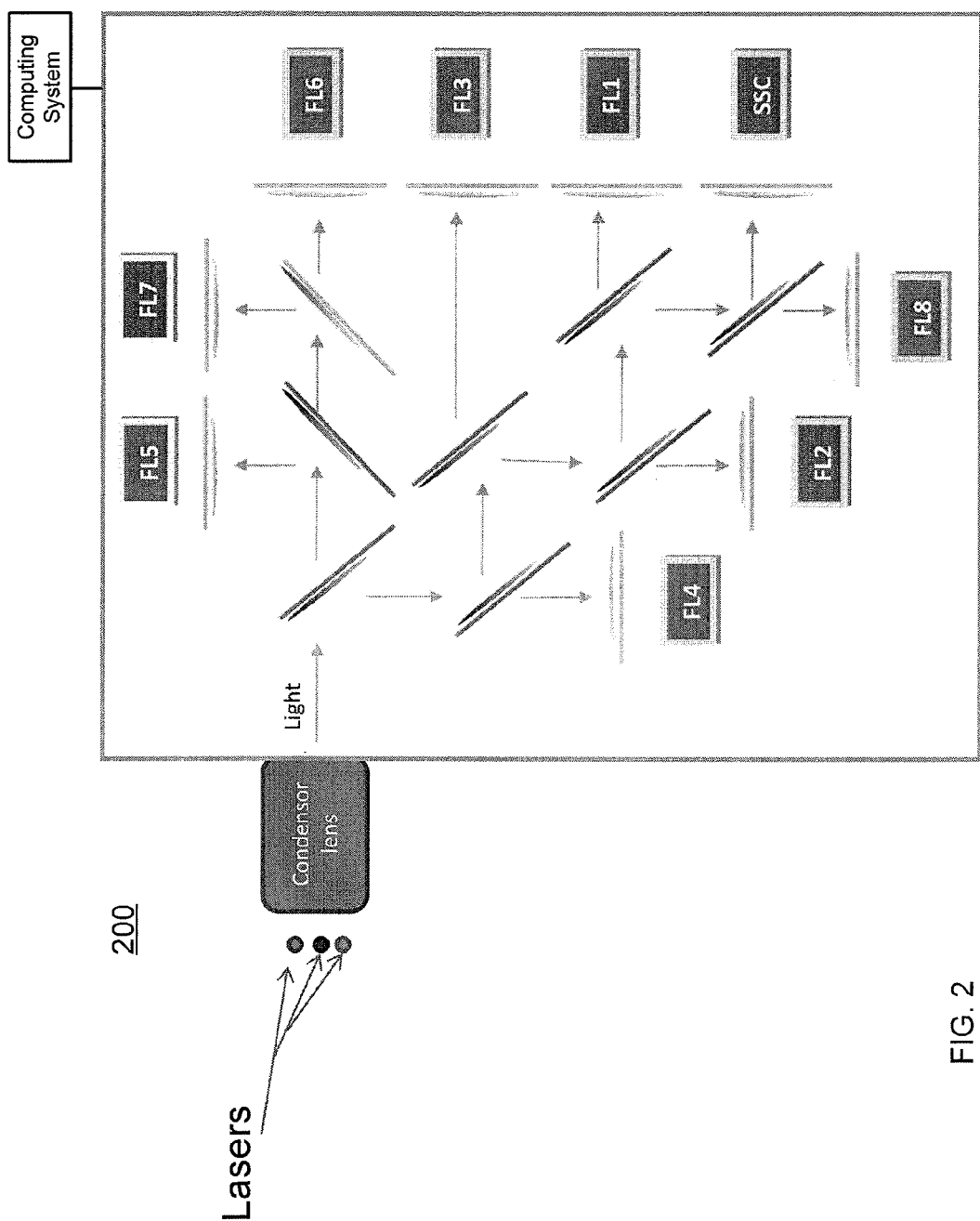

It should be understood that system 100 is a simplified embodiment, and other embodiments can include a plurality of detectors, with each detector being configured to process events from a plurality of lasers. FIG. 2 shows such a system which embodies such an arrangement.

FIG. 2 shows a cytometry system 200 having a plurality of detectors FL#, SSC, as shown. Each detector operates in a similar fashion to the detector 110, and includes similar gated sampling circuitry. However, an optics system 210 filters and directs certain wavelengths to each detector. In this embodiment, all detectors are configured to receive light from the condenser lens, however, user defined settings determine which detectors will be used. For example, the user may configure the computing system to use all or only a portion of the detectors. Each detector can be configured by a user, via a graphic user interface of the computing system, to be assigned to any laser. Further, each detector can be reassigned in a similar manner to different lasers. The user can also set the time of flight, and width gain for each detector. For example, detectors FL1, FL2, FL3, may all be assigned to two lasers. Each detector however, processes the light pulses in different manners as the optics system 210 filters different wavelengths of a respective light pulse to each detector.

The optics system 210 provides a high degree of flexibility and comparative information, as each detector can analyze and process a respective pulse of light in many different ways, and be arranged to do so in an efficient manner. Accordingly, each detector can process events from more than one laser source or from the same laser source without being permanently assigned (i.e., mechanically fixed) to a specific laser, and be reconfigured according to software controls implemented by a user.

Figure 3:
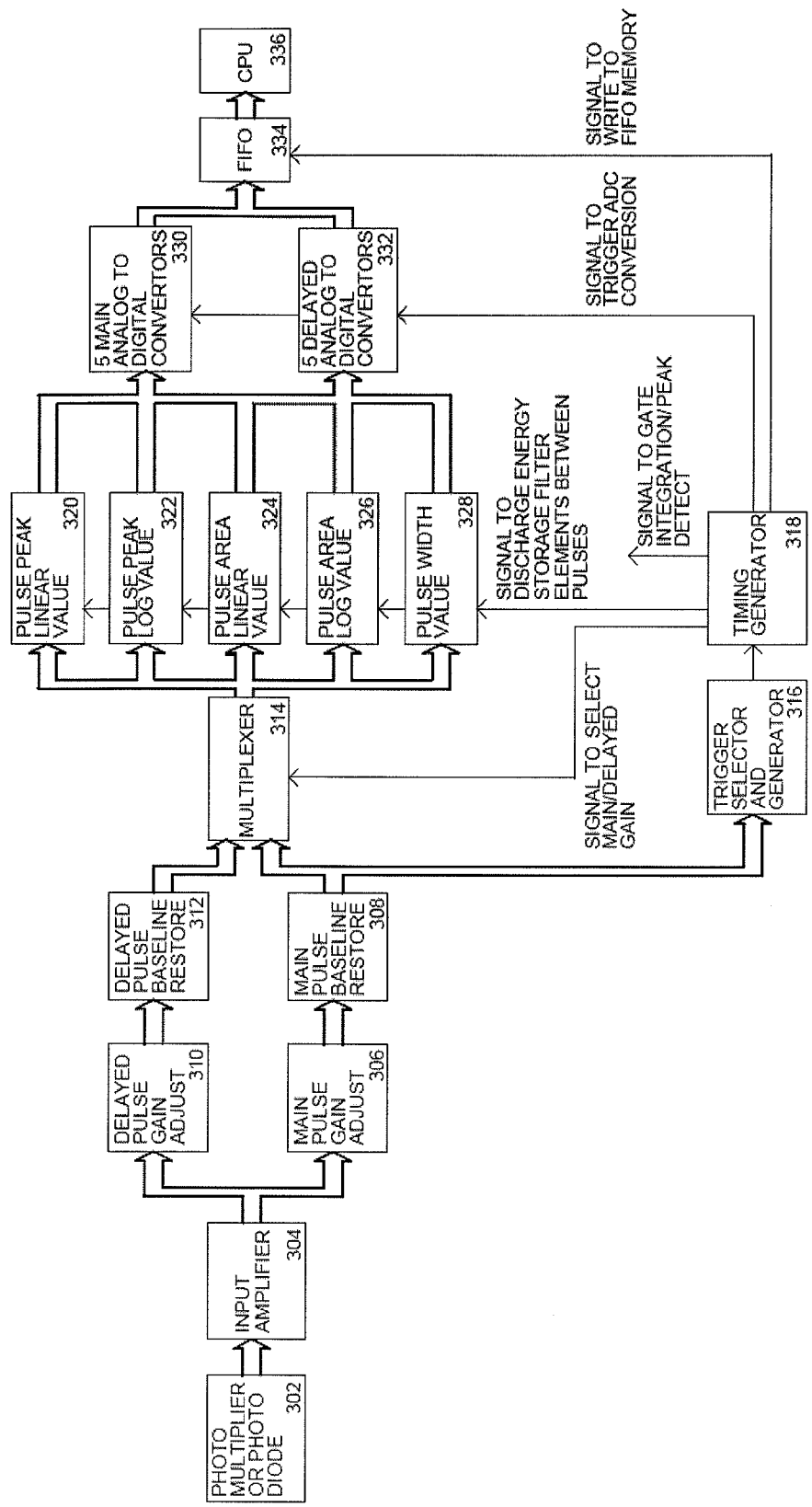
FIG. 3 is a simplified schematic of the operation and structure of a detector system, according to an embodiment of the invention.

FIG. 3 shows a simplified schematic of the operation and structure of a detector system 300, according to an embodiment of the invention. It should be understood that the detector system 300 can be used with any of the systems and methods disclosed herein. In some embodiments, aspects of the detector system 300 can be implemented as the detector 110, receiving circuit 115, and gated sampling circuitry 120 described with reference to FIG. 1. In other embodiments, respective aspects of a plurality of detector systems 300 can be implemented for each of the detectors FL#, SSC described with reference to FIG. 2.

A photodiode or photomultiplier 304 receives a light pulse which generates a pulse signal (e.g., current or voltage) in proportion to the light pulse. The pulse signal is then passed on to an input amplifier 304, as generally the pulse signal is very weak and requires amplification. The pulse signal is then processed through a main pulse gain path 306, 308 and a delayed pulse gain path 310, 312. For both paths, the gain of the signal is adjusted and its baseline restored to generate main pulse and delayed pulse signals. A multiplexer 314 selects the output for the respective gain paths.

The main pulse gain path also routes the main pulse signal to a trigger selector and generator 316, which in turn triggers a timing signal for generator 318 when a predetermined value is exceeded by the main pulse signal. The timing generator 318 then triggers an ON signal to the multiplexer 314 to route the main pulse signal to a plurality of gated sampling circuits. These circuits include a pulse peak linear value detector 320, a pulse peak logarithmic value detector 322, a pulse area linear value integrator 324, a pulse area logarithmic value integrator 326, and a pulse width value integrator 328. In some embodiments, other parameters may be detected as well, for example, pulse rise time, width to height ratio, Gaussian/non Gaussian, doublet. It should be understood that the detected parameters not being limited to width, area, and peak values, and in some embodiments such parameters may include any condition which is mathematically derivable from detected signal amplitude variation with time. The output values of these circuits are then passed to analog to digital (A/D) converters 330, 332, for both the main and delayed pulses. In some embodiments, a single A/D converter can be used to process both the main and delayed pulses. Further, in some embodiments the A/D converters 330, 332, or a single A/D converter, are respectively located between the input amplifier 304 and the main pulse gain path 306, 308 and the delayed pulse gain path 310, 312. Accordingly, the signals may be digitally converted directly after amplification and before being processed by the gated sampling circuits.

The digital output of the A/D converters 330, 332 may be saved and queued to a first-in-first-out memory component (FIFO) 334. The digital output is passed ultimately to a CPU 336 for further processing (e.g., histogram generation). The A/D and FIFO processes are also triggered by respective signals from the timing generator 318 at respective points in time during the duration of the ON signal.

The ON signal is generated only for the duration of the main pulse signal, and then is switched OFF. For example, this can be achieved by a switch of the timing generator 318 going from high to low, or vice-versa. During the OFF interval, another signal is generated by the timing generator 318 which causes the occurrence of an energy discharge of one or more energy storage filter elements of the gated sampling circuits. This is an important step, as pulse signals generated may vary greatly in magnitude. Accordingly, the residual energy from the signal of an initial pulse may otherwise mask a signal of a following pulse within the sampling circuitry, resulting in a faulty measurement. The energy discharge is timed to occur during the time of flight of a material (i.e., between the generation of the light pulses). The time of flight is known and calculated from the flow rate of the material and the spatial separation between the interrogations points of respective lasers. In some embodiments, the duration of the ON signal may be offset, fully or partially, from the duration of the main pulse signal.

The timing generator 318 then generates another signal, after the OFF interval, for the multiplexer 314 to route the output of the delayed pulse signal to the gated sampling circuits. The timing generator also sends another ON signal to the gated sampling circuits. This ON signal lasts for the duration of the delayed pulse signal. In some embodiments, the duration of the ON signal may be offset, fully or partially, from the duration of the delayed pulse signal. The output of the gated sampling circuits is then processed as described above with regards to the main pulse signal.

Figure 4:
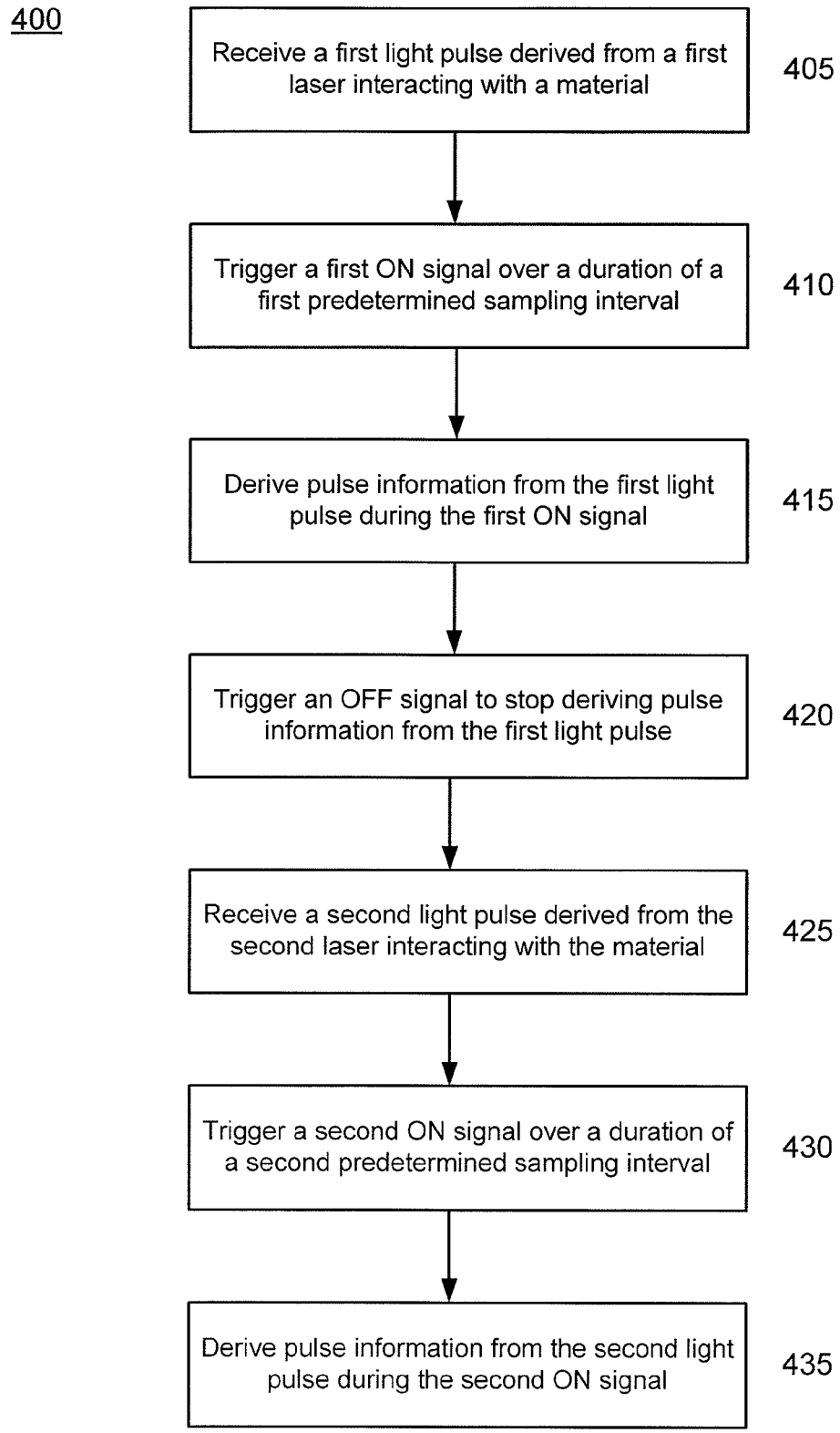
FIG. 4 is a flow chart for a method of operating a cytometry system, according to an embodiment of the invention.

FIG. 4 shows a method 400 for operating a cytometry system, according to an embodiment of the invention. It should be understood that method 400 can be implemented, in part or whole, in conjunction with any of the systems and/or subsystems disclosed herein.

At operation 405 a first light pulse signal is received by a cytometry measurement system. The light pulse signal is derived from the intersection of laser light with a material at an interrogation point, by collecting scattered (side and front) and/or fluoresced light which is routed via optics to a detector, e.g., a photodiode or photomultiplier. The photodiode or photomultiplier generates the light pulse signal which is typically a proportional signal (e.g., voltage, current) of the collected light. The light pulse signal can be routed through amplification circuitry and to signal processing circuitry (i.e., a sampling circuit). It should be understood that "light pulse signal" is intended to include informational signals derived from the collected reflected and/or fluoresced light which may be further processed by amplification, normalization, and/or digitizing circuits.

At operation 410 a first ON signal is triggered to activate the signal processing circuitry over a duration of a predetermined sampling interval. This may occur from the triggering of a high or low signal to the signal processing circuitry. During the sampling interval of the ON signal pulse information (e.g., linear/log pulse area/width, linear/log pulse peak) is derived from the first light pulse by the signal processing circuitry, as shown in operation 415. The pulse information can then be converted to digital information (if not already digitized from operation 405), queued in a buffer, and then further processed (e.g. histogram generation).

At operation 420, an OFF signal is triggered to stop deriving pulse information from the first light pulse. This may occur from the triggering of a high or low signal to the signal processing circuitry. The duration of the OFF signal corresponds to a time of flight interval of the material between the first laser and a spatially separated second laser. One or more energy storing filter elements of the signal processing circuitry can be discharged for the duration of the OFF signal to allow a following signal to be processed.

At operation 425 a second light pulse signal is derived from the second laser interacting with the material. This causes a trigger of a second ON signal over the duration of a second predetermined sampling interval, as shown in operation 430. Pulse information is then derived from the second light pulse during the second ON signal, as shown in operation 435.

Figure 5:
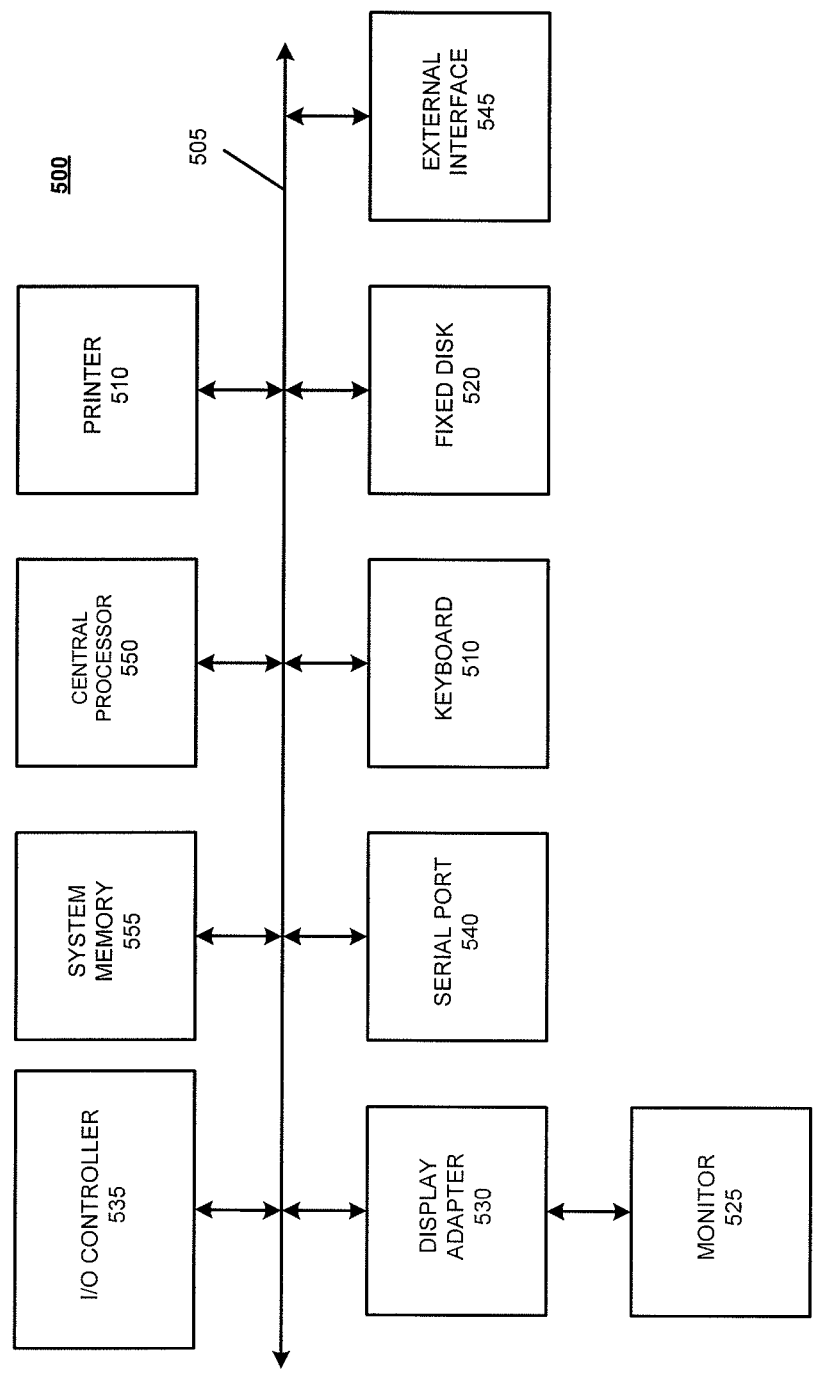
FIG. 5 is a schematic layout of a computing system for use with the methods and systems disclosed herein.

FIG. 5 is a schematic diagram of a computing system 500, for use with embodiments of the invention.

FIG. 5 is a high level block diagram of a computing system 500 that may be used to implement any of the entities or components described above, which may include one or more of the subsystems or components shown in FIG. 5. The subsystems shown in FIG. 5 are interconnected via a system bus 505. Additional subsystems such as a printer 510, keyboard 515, fixed disk 520, monitor 525, which is coupled to display adapter 530, and others are shown. Peripherals and input/output (I/O) devices, which couple to an I/O controller 535, can be connected to the computing apparatus 500 by any number of means known in the art, such as serial port 540. For example, serial port 540 or external interface 545 can be used to connect the computing apparatus 500 to a wide area network such as the Internet, a mouse input device, or a scanner. The interconnection via the system bus 505 allows the central processor 550 to communicate with each subsystem and to control the execution of instructions from system memory 555 or the fixed disk 520, as well as the exchange of information between subsystems. The system memory 555 and/or the fixed disk 520 may embody a computer readable medium.

It should be understood that the present invention as described above can be implemented in the form of control logic using computer software in a modular or integrated manner. Based on the disclosure and teachings provided herein, a person of ordinary skill in the art can know and appreciate other ways and/or methods to implement the present invention using hardware and a combination of hardware and software.

Any of the software components, user interfaces, or methods described in this application, may be implemented as software code to be executed by a processor using any suitable computer language such as, for example, Java, C++ or Perl using, for example, conventional or object-oriented techniques. The software code may be stored as a series of instructions, or commands on a computer readable medium, such as a random access memory (RAM), a read only memory (ROM), a magnetic medium such as a hard-drive or a floppy disk, or an optical medium such as a CD-ROM. Any such computer readable medium may reside on or within a single computational apparatus, and may be present on or within different computational apparatuses within a system or network.

The above description is illustrative and is not restrictive. Many variations of the invention will become apparent to those skilled in the art upon review of the disclosure. The scope of the invention should, therefore, be determined not with reference to the above description, but instead should be determined with reference to the pending claims along with their full scope or equivalents.

What is claimed is:

1. A cytometry system comprising:
a computing system;
a plurality of laser sources controlled by the computing system to emit laser light, each laser source being spatially separated along a flow stream path;
a light condenser for collecting a plurality of light pulses that are separated by time of flight intervals, each light pulse being derived from the spatially separated laser light intersecting material flowing in the flow stream path; and
a first detector configured to receive the plurality of light pulses from the light condenser, the first detector being coupled to sampling circuitry,
wherein the computing system is configured to operate the sampling circuitry to process each light pulse according to the time of flight intervals,
wherein the computing system is configured to turn the sampling circuitry OFF during the time of flight intervals by actively discharging residual energy of one or more energy storage filter elements of the sampling circuitry, wherein before each time of flight interval the residual energy is caused by filtering a prior light pulse, and wherein the residual energy caused by filtering the prior light pulse is actively discharged from the one or more energy storage filter element to prevent interference for processing a subsequent pulse by the sampling circuitry.

2. The cytometry system of claim 1, wherein the laser sources emit different wavelengths of laser light with respect to each other.

3. The cytometry system of claim 2, wherein at least one laser source comprises a plurality of collinear lasers.

4. The cytometry system of claim 1, wherein the computing system is configured to turn the sampling circuitry ON at least partially during the time of flight intervals.

5. The cytometry system of claim 1, wherein the computing system is configured to turn the sampling circuitry ON for pre-determined sampling intervals between the time of flight intervals and OFF during the time of flight intervals.

6. The cytometry system of claim 5, wherein the time of flight intervals are determined from a flow rate of the material and the distance between the spatially separated laser sources.

7. The cytometry system of claim 5, wherein the sampling circuitry is configured to only process a signal of each light pulse during the pre-determined sampling interval.

8. The cytometry system of claim 7, wherein the sampling circuitry is configured to discharge the one or more energy storage filter element at some time point when the signal of the light pulse is not being sampled.

9. The cytometry system of claim 1, further comprising:
a second detector configured to receive at least a portion of the plurality of light pulses from the light condenser, the second detector being coupled to its own sampling circuitry.

10. The cytometry system of claim 9, wherein the computing system is configured to turn respective sampling circuitries ON between the time of flight intervals and OFF during the time of flight intervals.

11. The cytometry system of claim 10, wherein the respective sampling circuitries are configured to discharge the one or more energy storage elements of the respective sampling circuitries at some time point when respective signals derived from the plurality of light pulses are not being sampled.

12. The cytometry system of claim 11, wherein the respective sampling circuitries are configured to process each light pulse by triggering pulse width integrators, logarithmic and linear pulse peak detectors, and logarithmic and linear pulse area integrators of respective signal processing circuitries.

13. The cytometry system of claim 11, wherein the respective signals are digitally converted before or after being processed by the respective signal processing circuitries.

14. A method for operating a cytometry system, the method comprising:
receiving a first light pulse derived from a first laser interacting with a material;
triggering a first ON signal over a duration of a first predetermined sampling interval;
deriving pulse information from the first light pulse signal during the first ON signal via signal processing circuitry;
triggering an OFF signal to stop the signal processing circuitry from deriving pulse information from the first light pulse signal, the OFF signal corresponding to a time of flight interval of the material between the first laser and a spatially separated second laser;
receiving a second light pulse signal derived from the second laser interacting with the material;
triggering a second ON signal over a duration of a second predetermined sampling interval; and
deriving pulse information from the second light pulse signal during the second ON signal,
wherein residual energy of at least one energy storing filter element of the signal processing circuitry is actively discharged during the OFF signal,
wherein before each time of flight interval the residual energy is caused by filtering the first light pulse, and wherein the residual energy caused by filtering the first light pulse is actively discharged from the energy storage filter element to prevent interference for processing the second light pulse by the sampling circuitry.

15. The method of claim 14, further comprising:
amplifying the first light pulse signal using a first amplifying circuit.

16. The method of claim 15, further comprising:
amplifying the second light pulse signal using a second amplifying circuit.

17. The method of claim 14, wherein at least one energy storing filter element of the signal processing circuitry is charged from the first light pulse signal during the first ON signal.

18. The method of claim 17, wherein the at least one energy storage filter element comprises a capacitor, inductor, or a processor or computer readable medium including a digital implementation of a filter.

19. The method of claim 14, wherein the at least one energy storing filter element of the signal processing circuitry is recharged from the second light pulse signal during the second ON signal.

20. The method of claim 14, wherein the time of flight interval is derived from a flow rate of the material between the spatial separation of the first laser and the second laser.

21. The method of claim 14, wherein deriving pulse information from the first and second light pulse signals respectively comprises triggering pulse width integrators, pulse peak detectors, and pulse area integrators of the signal processing circuitry.

22. The method of claim 14, wherein the pulse information respectively derived from the first and second light pulse signals is converted to digital signals.

* * * * *